US00PP37277P2

(12) United States Plant Patent
Ammerlaan

(10) Patent No.: US PP37,277 P2
(45) Date of Patent: Feb. 17, 2026

(54) ***GASTERALOE* PLANT NAMED 'OVROCKS15'**

(50) Latin Name: ***Gasteraloe carinata* x *Aloe aristata***
Varietal Denomination: OVROCKS15

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/831,560

(22) Filed: Apr. 17, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

U.S. PATENT DOCUMENTS

PP31,673 P2 * 4/2020 Ammerlaan ..... A01H 5/12
Plt./373

* cited by examiner

*Primary Examiner* — June Hwu
(74) *Attorney, Agent, or Firm* — Samuel R. McCoy, Jr.

(57) ABSTRACT

A new and distinct x*Gasteraloe* plant named 'OVROCKS15', which is characterized by a compact basal rosette of narrowly lanceolate, dark green foliage that is moderately covered with near-white protuberances arranged in highly irregular transverse rows across the laminar surface. The new variety has shown to be uniform and stable in the resulting generations from asexual propagation.

4 Drawing Sheets

Latin name of the genus and species: The Latin name of the genus and species of the novel variety disclosed herein is *Gasteraloe carinata x Aloe aristata*, which is synonymous with the nothogenus and species, *xGasteraloe beguinii*.

Variety denomination: The inventive variety of *Gasteraloe* hybrid disclosed herein has been given the variety denomination 'OVROCKS15'.

BACKGROUND OF THE INVENTION

Parentage: 'OVROCKS15' is a seedling selection resulting from the controlled pollination of an unnamed *Gasteria carinata* plant (not patented), the seed parent, with an unnamed *Aloe aristata* plant (not patented), the pollen parent. The crossing was made by the inventor in June of 2015 at a commercial greenhouse in Heerhugowaard, the Netherlands. In 2017, one seedling was observed which exhibited unique growth and foliage characteristics. After confirming the stability of the unique characteristics first observed, the new plant was selected for commercialization and given the name, 'OVROCKS15'.

Asexual Reproduction: Asexual reproduction of the new cultivar 'OVROCKS15', by way of rooting leaf cuttings, was first initiated in 2017 at the inventor's commercial greenhouse in Heerhugowaard, the Netherlands. Through eight subsequent generations, the unique features of this cultivar have proven to be stable and true to type.

SUMMARY OF THE INVENTION

The cultivar 'OVROCKS15' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS15'. These characteristics in combination distinguish 'OVROCKS15' as a new and distinct x*Gasteraloe* cultivar:

1. 'OVROCKS15' exhibits long, narrowly lanceolate foliage that is held tightly in a compact basal rosette; and
2. 'OVROCKS15' exhibits relatively dark green foliage that is moderately covered with very light greyed-green protuberances, generally appearing as a near-white coloration; and
3. 'OVROCKS15' exhibits foliar protuberances that are arranged in highly irregular transverse rows across the laminar surface; and
4. 'OVROCKS15' exhibits finely serrate foliar margins with very light greyed-green teeth, generally appearing as nearly white, with a greyed-purple mucronate lamina tip.

BOTANICAL DESCRIPTION OF THE PLANT

Figure 1:
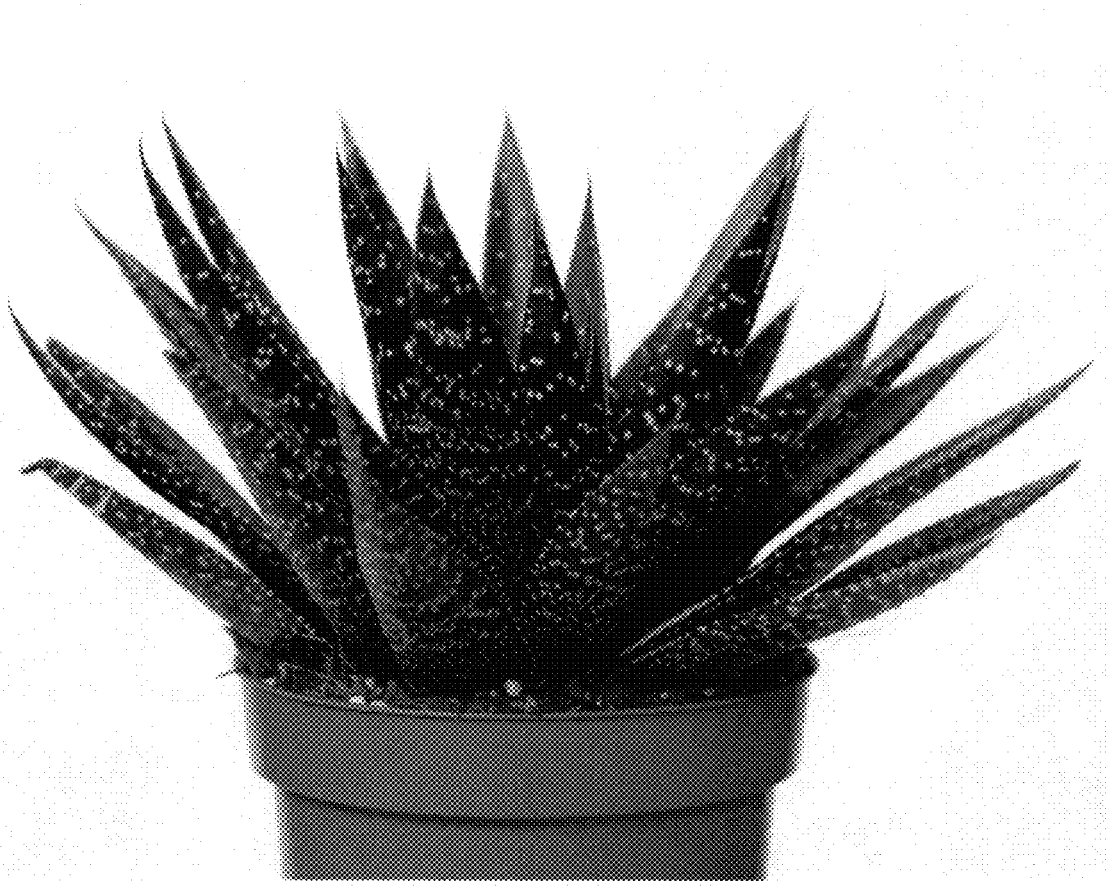
FIG. 1 illustrates, as nearly true as it is reasonably possible to make the same in color photographs of this type, an exemplary plant of 'OVROCKS15' grown in a commercial greenhouse in Heerhugowaard, the Netherlands. This plant is approximately 42-month-old, shown planted in a 12 cm container.
Figure 2:
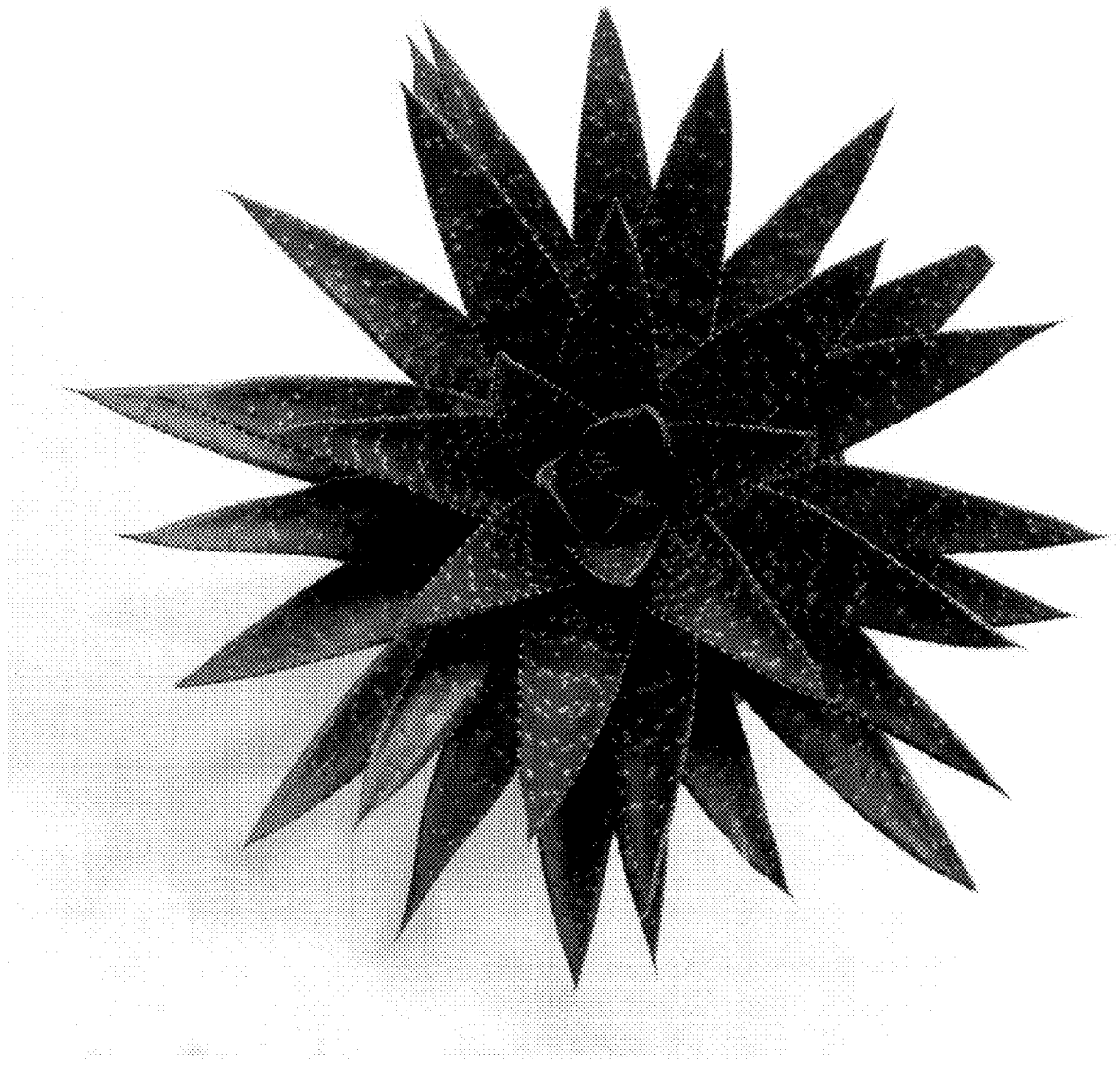
FIG. 2 illustrates, as nearly true as it is reasonably possible to make the same in color photographs of this type, the typical foliage arrangement of 'OVROCKS15'.
Figure 3:
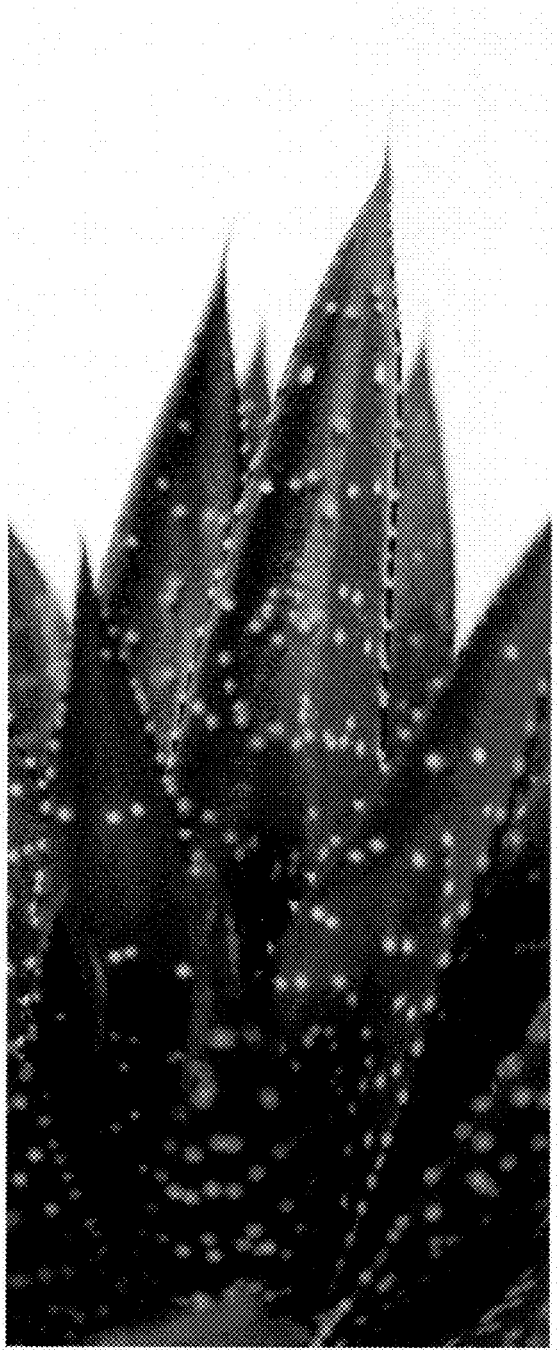
FIG. 3 illustrates, as nearly true as it is reasonably possible to make the same in color photographs of this type, the adaxial surface of the mature foliage 'OVROCKS15'.
Figure 4:
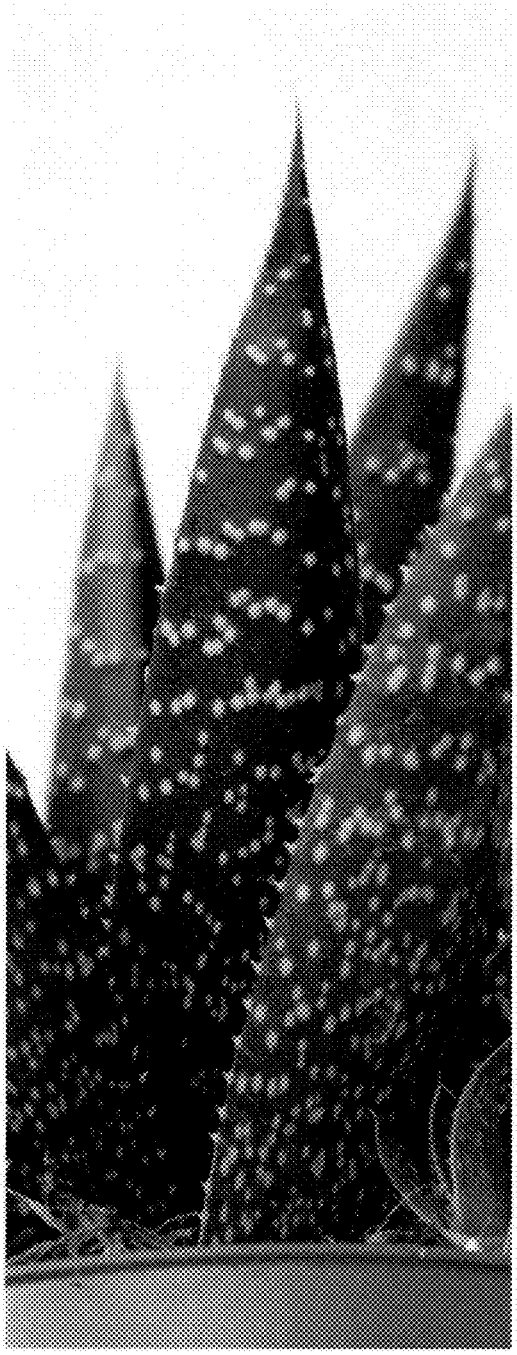
FIG. 4 illustrates, as nearly true as it is reasonably possible to make the same in color photographs of this type, the abaxial surface of the mature foliage 'OVROCKS15'.

The following observations and measurements made in October of 2024 describe averages from a sample set of six specimens of 42-month-old 'OVROCKS15' plants grown in 12 cm nursery containers at commercial greenhouse in Heerhugowaard, the Netherlands. Plants were produced using conventional greenhouse production protocols for x*Gasteraloe* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVROCKS15' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'OVROCKS15' and a comparison with the parents and closest known comparator is provided below.

Plant description:

*Growth habit*.—Succulent perennial with foliage growing in a stemless, non-branched basal rosette.

*Plant shape*.—Flattened globular.

*Height from soil level to top of foliar plane*.—13.3 cm.

*Plant spread*.—Average of 23.4 cm.

*Propagation*.—Type — Leaf cuttings. Time to initiate rooting — Approximately 21 days at 18 degrees Celsius. Crop time — Approximately 35 weeks to produce a marketable plant in a 10.5 cm container.

*Disease and pest resistance or susceptibility*.—Neither resistance nor susceptibility to typical *Gasteraloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosette; no main branches or lateral branches present.

Foliage:

*Arrangement*.—Spirally arranged in a rosette.

*Division*.—Simple.

*Attachment*.—Sessile.

*Quantity*.—40 leaves per rosette.

*Shape*.—Narrowly lanceolate, succulent foliage.

*Dimensions*.—12.4 cm long, 2.6 cm wide, and 0.9 cm thick, on average.

*Aspect*.—Slightly concaved.

*Attitude*.—Juvenile foliage at the center of the rosette is held upward to slightly outward; foliage becomes progressively more relaxed towards the outer whorls of mature foliage, at an average angle of 32.5 degrees from horizontal; lamina tips are reaching upwards at an average angle of 60 degrees from the lamina.

*Apex*.—Narrow acute, with a soft mucronate tip.

*Base*.—Broad cuneate.

*Margin*.—Finely serrate; teeth have an average length of 0.1 cm and are colored greyed-green, nearest to RHS 190D. Margins are not undulated or lobed.

*Texture, adaxial surface*.—Glabrous and moderately covered with orbicular protuberances irregularly arranged in transverse rows; protuberances are approximately 0.2 mm high and 1.25 mm in diameter at maturity.

*Texture, abaxial surface*.—Glabrous and densely covered with orbicular protuberances irregularly arranged in transverse rows; protuberances are approximately 0.1 cm high and 1.25 mm in diameter, at maturity. The distal one-third portion of the midrib bears protuberances which are modified into spines and arranged in a longitudinal row; spines have an average length of 0.8 mm.

*Luster, adaxial surface*.—Slightly glossy.

*Luster, abaxial surface*.—Slightly glossy.

*Color*.—Juvenile foliage, adaxial surface — Green, nearest to a blend of RHS NN137A and 139A, generally appearing as a dark green coloration yet slightly lighter than the mature foliage; and fading to yellow-green towards the base, nearest to RHS 137D, ultimately becoming RHS 152B proximally to the point of attachment; mucronate tips are colored greyed-purple, nearest to RHS 186D; protuberances are colored very light greyed-green, nearest to RHS 193D, generally appearing as a near-white coloration. Juvenile foliage, abaxial surface — Yellow-green, nearest to RHS 147A, and fading to grey-brown towards the base, nearest to RHS 199B; mucronate tips are colored greyed-purple, nearest to RHS 186D; protuberances are colored very light greyed-green, nearest to RHS 193D, generally appearing as a near-white coloration. Serrate teeth along the distal one-third of the midrib are greyed-green, nearest to a blend of RHS 190C and 190D. Mature foliage, adaxial surface — Yellow-green to greyed-green, nearest to a blend of RHS 147A and N189A, generally appearing as a dark green coloration; fading to greyed-green towards the base, nearest to RHS 191A; mucronate tips are colored greyed-purple, nearest to RHS 186D; protuberances are colored greyed-green, nearest to RHS 190A and 190B, generally appearing as a near-white coloration. Mature foliage, abaxial surface — Yellow-green to greyed-green, nearest to a blend of RHS 147A and N189A, and fading to yellow-green towards the base, nearest to RHS 144A, ultimately becoming grey-brown, nearest to RHS 199B, proximally to the point of attachment; mucronate tips are colored greyed-purple, nearest to RHS 186D; protuberances are colored greyed-green, nearest to a combination of RHS 190A, 190B, and 190C, generally appearing as a near-white coloration. Serrate teeth along the distal one-third of the midrib are greyed-green, nearest to a blend of RHS 190C and 190D, generally appearing as a near-white coloration.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'OVROCKS15' differ from the seed parent, an unnamed *Gasteria carinata* plant (not patented), in the following characteristics described in Table 1 below.

TABLE 1

Comparison Between 'OVROCKS15' and The Seed Parent.

| Characteristic | 'OVROCKS15' | The Seed Parent |
|---|---|---|
| Plant size. | Smaller than the seed parent. | Larger than 'OVROCKS15'. |
| General coloration of the mature foliage. | Yellow-green to greyed-green. | Green. |
| Foliage length and arrangement. | Shorter leaves in a whorled basal rosette. | Taller leaves than 'OVROCKS15', arranged in a distichous leaf arrangement on a singular plane with secondary shoots growing from the base of the plant. |
| Leaf shape. | Thin lanceolate leaves with narrow acute apices and a mucronate tip. | Thicker and broader lanceolate succulent leaves than 'OVROCKS15' with obtuse apices. |

Plants of the new cultivar 'OVROCKS15' differ from the pollen parent, an unnamed *Aloe aristata* plant (not patented), in the following characteristics described in Table 2 below.

TABLE 2

Comparison Between 'OVROCKS15' and The Pollen Parent.

| Characteristic | 'OVROCKS15' | The Pollen Parent |
|---|---|---|
| General coloration of the mature foliage. | Darker shade of green than the pollen parent. | Lighter shade of green than 'OVROCKS15'. |
| Foliage shape and dimensions. | Lanceolate succulent foliage that is longer on average than the pollen parent. | Ovate succulent foliage that is shorter on average than 'OVROCKS15'. |
| Abundance and attitude of foliage. | Less leaves that rest more relaxed than the pollen parent. | More leaves in a tighter compact basal rosette than 'OVROCKS15'. |

TABLE 2-continued

Comparison Between 'OVROCKS15' and The Pollen Parent.

| Characteristic | 'OVROCKS15' | The Pollen Parent |
|---|---|---|
| Prominence of leaf protuberances. | Less prominent than 'OVROCKS06'. | More prominent than 'OVROCKS15'. |
| Leaf margins. | Spines of 'OVROCKS15' are evenly distributed and spaced in serrate margins. | The quantity of spines on the pollen parent's serrate margins are higher and more prominent than 'OVROCKS15'. |

COMPARISONS WITH THE CLOSEST KNOWN COMPARATOR

Plants of the new cultivar 'OVROCKS15' differ from the closest known commercial comparator, the x*Gasteraloe* plant called 'OVROCKS06' (U.S. Plant Pat. No. 31,673) in the following characteristics described in Table 3 below.

TABLE 3

Comparison Between 'OVROCKS15' and 'OVROCKS06'

| Characteristic | 'OVROCKS15' | 'OVROCKS06' |
|---|---|---|
| General coloration of the mature foliage. | Darker shade of green than 'OVROCKS06'. | Lighter shade of green than 'OVROCKS15'. |
| Foliage shape and dimensions. | Narrowly lanceolate succulent foliage that is longer on average than 'OVROCKS06'. | Ovate succulent foliage that is shorter on average than 'OVROCKS15'. |
| Abundance and attitude of foliage. | 40 leaves per rosette; more compact and upright than 'OVROCKS06'. | 32 leaves per rosette; more relaxed and spreading than 'OVROCKS15'. |
| Prominence of leaf protuberances. | More prominent than 'OVROCKS06'. | Less prominent than 'OVROCKS15'. |
| Size of the foliar protuberances. | Larger than 'OVROCKS06'. | Smaller than 'OVROCKS15'. |
| Color of foliar protuberances. | Very light greyed-green, generally appearing as a near-white coloration. | Yellow-green |
| Arrangement and density of foliar protuberances. | Arranged in irregular transverse rows across the lamina; fewer protuberances per leaf relative to 'OVROCKS06'. | Random, with no apparent order; significantly more protuberances than 'OVROCKS15'. |

That which is claimed is:

1. A new and distinct variety of x*Gasteraloe* hybrid plant named 'OVROCKS15', substantially as described and illustrated herein.

* * * * *